United States Patent
Chen et al.

(10) Patent No.: US 10,577,394 B2
(45) Date of Patent: Mar. 3, 2020

(54) GANIRELIX PRECURSOR AND METHOD FOR PREPARING GANIRELIX ACETATE BY USING THE SAME

(71) Applicant: HYBIO PHARMACEUTICAL CO., LTD., Shenzhen (CN)

(72) Inventors: Youjin Chen, Shenzhen (CN); Jian Liu, Shenzhen (CN); Yaping Ma, Shenzhen (CN); Jiancheng Yuan, Shenzhen (CN)

(73) Assignee: HYBIO PHARMACEUTICAL CO., LTD., Shenzhen, Guangdong (CN)

( * ) Notice: Subject to any disclaimer, the term of this patent is extended or adjusted under 35 U.S.C. 154(b) by 216 days.

(21) Appl. No.: 15/318,356

(22) PCT Filed: Jun. 12, 2015

(86) PCT No.: PCT/CN2015/081311
§ 371 (c)(1),
(2) Date: Dec. 12, 2016

(87) PCT Pub. No.: WO2015/188774
PCT Pub. Date: Dec. 17, 2015

(65) Prior Publication Data
US 2017/0121371 A1    May 4, 2017

(30) Foreign Application Priority Data
Jun. 13, 2014 (CN) .......................... 2014 1 0265647

(51) Int. Cl.
| | | |
|---|---|---|
| C07K 7/23 | (2006.01) |
| C07K 1/107 | (2006.01) |
| C07K 1/06 | (2006.01) |
| C07K 1/04 | (2006.01) |
| C07K 7/06 | (2006.01) |

(52) U.S. Cl.
CPC .................. *C07K 7/23* (2013.01); *C07K 1/04* (2013.01); *C07K 1/06* (2013.01); *C07K 1/107* (2013.01); *C07K 7/06* (2013.01); Y02P 20/55 (2015.11)

(58) Field of Classification Search
None
See application file for complete search history.

(56) References Cited

U.S. PATENT DOCUMENTS

| 5,212,288 A | 5/1993 | Nestor, Jr. et al. |
| 5,767,082 A | 6/1998 | Nestor, Jr. et al. |
| 2004/0266695 A1 | 12/2004 | Bernd et al. |

FOREIGN PATENT DOCUMENTS

| CN | 1348462 A | 5/2002 |
| CN | 102584945 A | 7/2012 |
| CN | 102993274 | * 3/2013 |
| CN | 104231055 A | 12/2014 |
| CN | 104844694 | 8/2015 |
| EP | 0301850 A2 | 2/1989 |
| EP | 0443532 A2 | 8/1991 |

OTHER PUBLICATIONS

English translation from WIPO for PCT International Preliminary Report on Patentability (Chapter I) with Written Opinion from PCT/CN2015/081311 dated Dec. 15, 2016.
Extended European search report from corresponding European Patent Application No. 15805742.2 dated Dec. 12, 2017.
Thomas Beckers et al. "Structure-Function Studies of Linear and Cyclized Peptide Antagonists of the GnRH Receptor", Biochemical and Biophysical Research Communications, vol. 289, No. 3, Dec. 1, 2001, pp. 653-663, Elsevier Science.
International Search Report for PCT/CN2015/081311 dated Sep. 22, 2015.
Written Opinion of the International Search Authority for PCT/CN2015/081311 dated Sep. 22, 2015 and its English machine translation from Bing translator.
Horn, F. et al., "Intracellular Responses to Gonadotropin-Releasing Hormone in a Clonal Cell Line of the Gonadotrope Lineage", Molecular Endocrinology, vol. 5, No. 3, Mar. 31, 1991, ISSN: 0888-8809, pp: 347-355, and table 2.
From CN201210028919.2 (now published as CN 102584945A), First Office Action dated Apr. 25, 2013, and its English translation from Espacenet's Global Dossier.
From CN201210028919.2 (now published as CN 102584945A), Second Office Action dated Dec. 19, 2013, and its English translation from Espacenet's Global Dossier.
The 9-Fluorenylmethoxycarbonyl Amino-Protecting Group, Carpino et al., Journal of Organic Chemistry, vol. 37, No. 22, Apr. 10, 1972.
Synthesis of L-Homoarginine Monohydrochloride, Zou et al., Chemical Industry Times, vol. 20, No. 7, Jul. 7, 2006 with a machine translation from Bing Translator.
International Preliminary Report on Patentability for PCT/CN2015/081311 dated Dec. 15, 2016 including the Written Opinion of the International Search Authority dated Sep. 22, 2015.

(Continued)

*Primary Examiner* — James H Alstrum-Acevedo
*Assistant Examiner* — Tara L Martinez
(74) *Attorney, Agent, or Firm* — Ladas & Parry, LLP

(57) ABSTRACT

Disclosed is a method for preparing ganirelix acetate. The method includes the following steps: respectively replacing Fmoc-HArg(Et)$_2$-OH and Fmoc-D-HArg(Et)$_2$-OH by employing Fmoc-Lys(Boc)-OH and Fmoc-D-Lys(Boc)-OH or Fmoc-Lys(Alloc)-OH and Fmoc-D-Lys(Alloc)-OH; synthesizing a ganirelix precursor I or ganirelix precursor II-peptide resin in advance; and then respectively performing modifications and treatments on side chain amino groups of Lys and D-Lys in the precursor I or the precursor II-peptide resin to obtain ganirelix acetate. The ganirelix acetate synthesized therefrom is high in purity, has few impurities and a relatively low cost, and is suitable for large-scale production.

20 Claims, 2 Drawing Sheets

(56) References Cited

OTHER PUBLICATIONS

Written Opinion of the International Search Authority for PCT/CN2015/081311 dated Sep. 22, 2015 and its English machine translation from WIPO.
Office action from Chinese Patent Application No. 201410265647 dated May 9, 2018 with search report, and its English translation.
Office action from Japanese Patent Application No. 2017517175 dated May 14, 2019, and its English translation.
"Manufacturing method of Ganirelix Precursor and Ganirelix Acetate Using the Same," Basics of Peptide Synthesis an Experimentents, Maruzen Co., Ltd., 1985, pp. 247-249.

* cited by examiner

| | Injection | RT | Area | % Area | Height |
|---|---|---|---|---|---|
| 1 | 1 | 14.782 | 9526 | 0.11 | 542 |
| 2 | 1 | 15.375 | 8279212 | 99.80 | 365200 |
| 3 | 1 | 16.255 | 7342 | 0.09 | 397 |
| Mean | | 15.471 | | | |
| Std. Dev. | | 0.741 | | | |
| % RSD | | 4.79 | | | |

GANIRELIX PRECURSOR AND METHOD FOR PREPARING GANIRELIX ACETATE BY USING THE SAME

CROSS-REFERENCE TO RELATED APPLICATIONS

The present application is the U.S. national phase of PCT Application PCT/CN2015/081311 filed on Jun. 12, 2015, which claims the priority of the Chinese patent application No. 201410265647.7 filed on Jun. 13, 2014, the disclosures of which are incorporated herein by reference in their entireties.

FIELD OF THE INVENTION

The present disclosure relates to the technical field of pharmaceutical synthesis, and more particularly, to a ganirelix precursor and a method for preparing ganirelix acetate by using the ganirelix precursor.

BACKGROUND

Ganirelix acetate, with a chemical name of N-acetyl-3-(2-napthyl)-D-alanyl-4-chloro-D-phnylalanyl-3-(3-pyridyl)-D-alanyl-L-tyrosyl-$N_9,N_{10}$diethyl-D-homoarginyl-L-leucyl-$N_9,N_{10}$-diethyl-L-homoarginyl-L-prolyl-D-alanylamide acetate, a molecular formula of $C_{80}H_{113}ClN_{18}O_{13}$, a relative molecular mass of 1570.3 and a CAS registration number of 123246-29-7, has a chemical structure shown in the following formula:

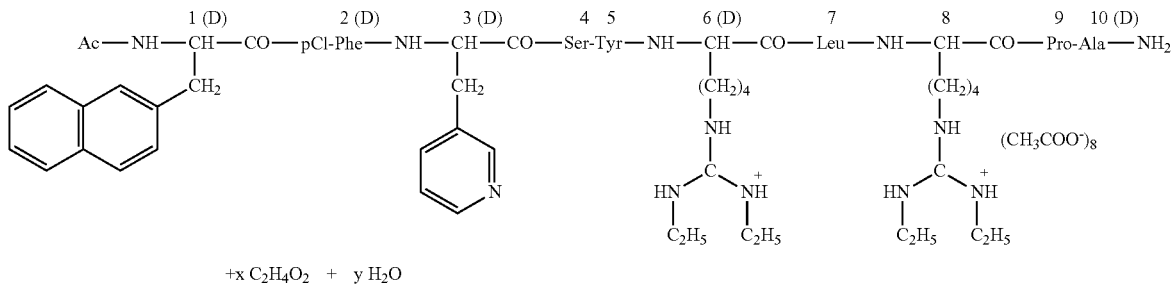

Ganirelix acetate is a synthesized decapeptide compound similar to endogenous gonadotropin-releasing hormone (GnRH) (also called luteinizing hormone-releasing hormone, LHRH) and an antagonist of GnRH, and can competitively antagonize the GnRH receptor of gonadotropin, so as to mutate an approach, and rapidly and reversibly inhibit secretion of gonadotropin (luteinizing hormone LH and follicle stimulating hormone FSH). Ganirelix acetate has a more significant inhibitory effect on luteinizing hormone LH secretion than on FSH secretion, so as to reduce generation of sex hormone. By inhibiting induced fluctuation of LH by GnRH in a medium cycle, ganirelix acetate can inhibit ovulation, oocyte meiosis, and luteinization. For women suffering from an ovarian hyperstimulation syndrome, ganirelix acetate can prevent LH fluctuation and related simulations and improve implantation and pregnancy ratios. Therefore, ganirelix acetate has a high medicinal value and a broad market prospect. Currently, methods for synthesizing ganirelix acetate mainly include a conventional Boc stationary phase synthesizing method employed in U.S. Pat. No. 5,767,082 and a Fmoc stationary phase synthesizing method employed in CN 102584945A. HF needs to be used for cracking in the Boc stationary phase synthesizing method employed in U.S. Pat. No. 5,767,082, thereby greatly polluting the environment and not facilitating production. Fmoc-HArg(Et)$_2$-OH and Fmoc-D-HArg(Et)$_2$-OH need to be used as raw materials in the Fmoc stationary phase synthesizing method employed in CN 102584945A. The two kinds of amino acids have high synthesizing costs, so as not to facilitate large-scale production. In addition, the two kinds of amino acids are easy to decompose, while multiple times of coupling reactions are needed after the two kinds of amino acids are connected to a resin, and as a result, many impurities are generated.

SUMMARY OF THE INVENTION

In order to overcome the above defects existing in the prior art, the present disclosure discloses a method for preparing ganirelix acetate without using HF or employing Fmoc-HArg(Et)$_2$-OH and Fmoc-D-HArg(Et)$_2$-OH as raw materials. Therefore, the present disclosure provides, in one aspect, a ganirelix precursor I and a preparation method thereof, and a method for preparing ganirelix acetate by using the precursor I, wherein the precursor I has a structure as shown below: Ac-D-2-Nal-D-Phe(4-Cl)-D-3-Pal-Ser-Tyr-D-Lys-Leu-Lys-Pro-D-Ala-NH$_2$.

The preparation method of the precursor I includes the following steps:
(1) reacting Fmoc-D-Ala-OH with a resin to obtain a Fmoc-D-Ala-resin;
(2) coupling the Fmoc-D-Ala-resin to other amino acids with Fmoc protecting group one by one, followed by acetylation to obtain a ganirelix precursor I-peptide resin; and
(3) subjecting the ganirelix precursor I-peptide resin to a cleavage reaction to obtain the ganirelix precursor I.

In a preferred embodiment, the other amino acids with Fmoc protecting group in step (2) include Fmoc-Pro-OH, Fmoc-Lys(Boc)-OH, Fmoc-Leu-OH, Fmoc-D-Lys(Boc)-OH, Fmoc-Tyr(tBu)-OH, Fmoc-Ser(tBu)-OH, Fmoc-D-Pal-OH, Fmoc-D-Cpa-OH and Fmoc-D-Nal-OH, respectively.

The method for preparing ganirelix acetate by using the precursor I includes the following steps:
(1) preparing the ganirelix precursor I with the above structure;
(2) performing modifications on side chain amino groups of Lys and D-Lys in the ganirelix precursor I obtained in step (1) to obtain crude ganirelix; and
(3) subjecting the crude ganirelix obtained in step (2) to purification, salt conversion and lyophilization to obtain pure ganirelix acetate.

In a preferred embodiment, a reagent used for performing modifications on side chain amino groups in step (2) is ethylamino ethylimino methanesulfonic acid, a solvent used is DMF, NMP, DMSO, acetonitrile, THF, 1,4-dioxane or MeOH, and a base used is DIPEA, Et$_3$N, TMP, pyridine, NaHCO$_3$ or Na$_2$CO$_3$.

In another aspect, the present disclosure provides a ganirelix precursor II-peptide resin and a preparation method thereof, and a method for preparing ganirelix acetate by using the above precursor II-peptide resin, wherein the precursor II-peptide resin has a structure as shown below:
Ac-D-2-Nal-D-Phe(4-Cl)-D-3-Pal-Ser(tBu)-Tyr(tBu)-D-Lys-Leu-Lys-Pro-D-Ala-resin.

The preparation method of the precursor II-peptide resin includes the following steps:
(1) reacting Fmoc-D-Ala-OH with a resin to obtain an Fmoc-D-Ala-resin;
(2) coupling the Fmoc-D-Ala-resin to other amino acids of with Fmoc protecting group one by one, followed by racetylation and lysine deprotection to obtain a ganirelix precursor II-peptide resin.

In a preferred embodiment, the other amino acids with Fmoc protecting group in step (2) include Fmoc-Pro-OH, Fmoc-Lys(Alloc)-OH, Fmoc-Leu-OH, Fmoc-D-Lys(Alloc)-OH, Fmoc-Tyr(tBu)-OH, Fmoc-Ser(tBu)-OH, Fmoc-D-Pal-OH, Fmoc-D-Cpa-OH and Fmoc-D-Nal-OH, respectively.

The method for preparing ganirelix acetate by using the precursor II-peptide resin includes the following steps:
(1) preparing the ganirelix precursor II-peptide resin with the above structure;
(2) performing modifications on side chain amino groups of Lys and D-Lys in the ganirelix precursor II-peptide resin obtained in step (1) to obtain crude ganirelix; and
(3) subjecting the crude ganirelix obtained in step (2) to purification, salt conversion and lyophilization to obtain pure ganirelix acetate.

In a preferred embodiment, a reagent used for performing modifications on side chain amino groups in step (2) is ethylamino ethylimino methanesulfonic acid, a solvent used is DMF, DCM or DMSO, and a base used is DIPEA, Et$_3$N or NMM. In the method for preparing the ganirelix precursor I and the ganirelix precursor II-peptide resin, Rink Amide resin, Rink Amide AM resin or Rink Amide MBHA resin are preferably employed.

In the above method for preparing the ganirelix precursor I and the method for preparing ganirelix acetate by using the ganirelix precursor II-peptide resin, the ratio of cleavage reagents employed in the cleavage reaction is preferably TFA:Anisole:Thioanisole:TIS:H$_2$O:EDT=90-95:0-5:0-3:0-3:0-5:0-2(V/V), more preferably TFA:Anisole:Thioanisole:EDT=90:5:3:2(V/V).

In a process for preparing ganirelix acetate in the present disclosure, an HPLC method is employed to perform purification on the crude ganirelix and then salt conversion is performed, and the method includes the following specific steps:
(1) sample treatment: dissolving solid crude ganirelix peptide with acetonitrile and purified water in a volume ratio of 1:3, completely dissolving the sample by ultrasonic and then filtering with a filter membrane, and collecting filtrate for later use;
(2) HPLC purification: performing gradient elution with a mobile phase varying from 75% A+25% B to 65% A+35% B, wherein octylsilane-bonded silica serves as the stationary phase of the chromatographic column, the solubility of a sodium perchlorate solution in the phase A of the mobile phase is 20 mM, pH is adjusted to 1.5 with phosphoric acid, and acetonitrile serves as the phase B.
(3) salt conversion: after performing gradient elution with 95% A+5% B serving as a mobile phase for 20 min, varying the mobile phase from 95% A+5% B to 50% A+50% B within 2 min, and then performing gradient elution with 50% A+50% B serving as a mobile phase, wherein a reverse phase C8 chromatographic packing serves as a stationary phase of the chromatographic column, the phase A of the mobile phase is 0.20% glacial acetic acid (V/V) solution, and the phase B is chromatographic grade acetonitrile.

It can be seen from the above that as compared with the prior art, in the present disclosure, Fmoc-Lys(Boc)-OH and Fmoc-D-Lys(Boc)-OH or Fmoc-Lys(Alloc)-OH and Fmoc-D-Lys(Alloc)-OH are respectively employed to replace Fmoc-HArg(Et)$_2$-OH and Fmoc-D-HArg(Et)$_2$-OH, and the ganirelix acetate precursor I or the ganirelix acetate precursor II-peptide resin are synthesized in advance, then modifications and treatments are respectively performed on the Lys and D-Lys in the precursor I or the precursor II-peptide resin to obtain ganirelix acetate. HF is not required to be used in the preparation method of the present disclosure, which greatly reduce pollution to the environment, and Fmoc-HArg(Et)$_2$-OH and Fmoc-D-HArg(Et)$_2$-OH are not required to be used. The synthesized ganirelix has high purity, few impurities and a relatively low cost, and is suitable for large-scale production.

DETAILED DESCRIPTION OF THE INVENTION

Figure 1:
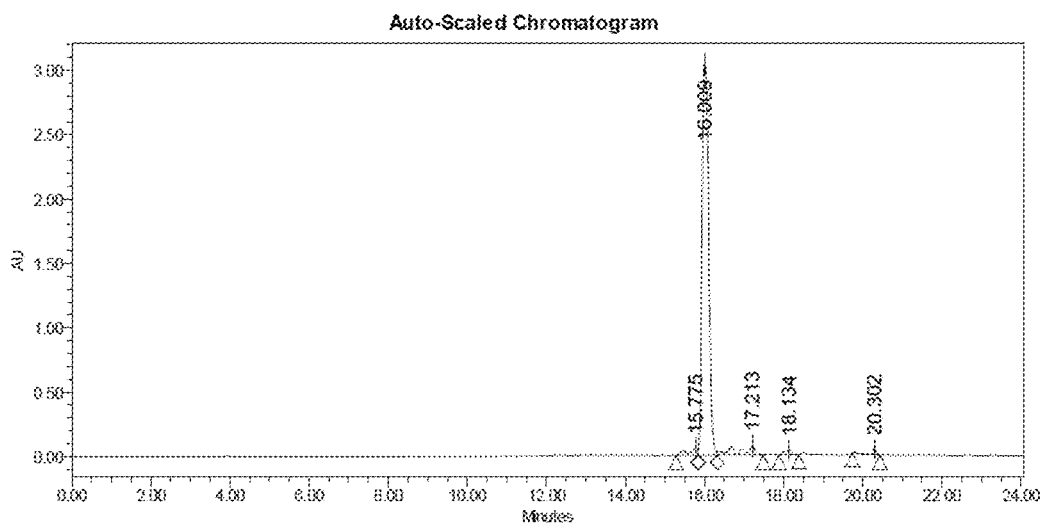
FIG. 1 is a peptide spectrum of the ganirelix precursor-I prepared from example 1.

The present disclosure will be further illustrated in detail by the following examples, which are intended to illustrate, but not to limit the present disclosure. It should be noted that for a person skilled in the art, various improvements and modifications may be made to the present disclosure without departing from the principles of the present disclosure, and these improvements and modifications also fall into the protection scope of the present disclosure.

Meanings of abbreviations used in the present disclosure are listed in the following table.

| English abbreviation | Chinese meaning |
| --- | --- |
| DIC | N,N'-diisopropylcarbodiimide |
| DCM | dichloromethane |
| Et$_2$O | anhydrous ether |
| MeOH | methanol |
| EA | ethyl acetate |
| H$_2$O | water |
| NaHCO$_3$ | sodium bicarbonate |
| THF | tetrahydrofuran |
| PyBOP | benzotriazol-1-yl-oxytripyrrolidino-phosphonium hexafluorophosphate |
| DIPEA | N,N-diisopropylethylamine |
| HOBt | 1-hydroxybenzotriazole |
| TFA | trifluoroacetic acid |
| TIS | triisopropylsilane |
| EDT | ethanedithiol |
| DMF | N,N-dimethylformamide |
| 20% DBLK | 20% hexahydropyridine(v)/N,N-dimethylformamide(v) |

Example 1: Synthesis of Ganirelix Precursor I

1. Preparation of Fmoc-D-Ala-Rink Amide Resin (1) Small-Scale Experiment

The following steps are included: placing 10 g of Rink Amide resin with a substitution degree of 0.5 mmol/g into a solid-phase reaction column, performing DMF washing twice, performing DMF swelling for 30 min and DBLK deprotection twice for 10 min and 15 min respectively, and performing DMF washing six times, ninhydrin test being positive;

dissolving Fmoc-D-Ala-OH (4.67 g, 15 mmol) and HOBt (2.13 g, 15.75 mmol) in 40 ml of DMF, adding DIC (2.47 ml, 15.75 mmol) for activating for 5 min under the condition of an ice bath, adding the activated solution to the solid-phase reaction column and stirring for reaction for 2 h with nitrogen, ninhydrin test being negative; draining the reaction solution, performing DMF washing three times, performing DBLK deprotection twice for 5 min and 7 min respectively, and performing DMF washing six times, ninhydrin test being positive.

(2) Amplification Experiment

The following steps are included: placing 100 g of Rink Amide resin with a substitution degree of 0.5 mmol/g into a solid-phase reaction column, performing DMF washing twice, and performing DMF swelling for 30 min and DBLK deprotection twice for 10 min and 15 min respectively, and performing DMF washing six times, ninhydrin test being positive;

dissolving Fmoc-D-Ala-OH (46.7 g, 150 mmol) and HOBt (21.3 g, 157.5 mmol) in 400 ml of DMF, adding DIC (2.47 ml, 157.5 mmol) for activating for 5 min under the condition of an ice bath, adding the activated solution to a solid-phase reaction column and stirring for reaction for 2 h with nitrogen, ninhydrin test being negative; draining the reaction solution, performing DMF washing three times, performing DBLK deprotection twice for 5 min and 7 min respectively, and performing DMF washing six times, ninhydrin test being positive.

2. Coupling of Other Amino Acids with Fomc Protection Group, and Obtaining the Ganirelix Precursor I-Peptide Resin after Acetylation (1) Small-Scale Experiment The following steps are included: repeating the foregoing steps, and sequentially coupling Fmoc-Pro-OH, Fmoc-Lys(Boc)-OH, Fmoc-Leu-OH, Fmoc-D-Lys(Boc)-OH, Fmoc-Tyr(tBu)-OH, Fmoc-Ser(tBu)-OH, Fmoc-D-Pal-OH and Fmoc-D-Cpa-OH one by one;

dissolving Fmoc-D-Nal-OH (6.54 g, 15 mmol) and HOBt (2.13 g, 15.75 mmol) in 40 ml of DMF, adding DIC (2.47 ml, 15.75 mmol) for activating for 5 min under the condition of an ice bath, adding the activated solution to a solid-phase reaction column and stirring for reaction for 2 h with nitrogen, ninhydrin test being negative; draining the reaction solution, performing DMF washing three times, performing DBLK deprotection twice for 5 min and 7 min respectively, performing DMF washing six times, and performing DCM washing twice, ninhydrin test being positive;

dissolving acetic anhydride (10.2 g, 100 mmol) and pyridine (7.9 g, 100 mmol) in 30 ml of DCM, adding the solution to a solid-phase reaction column at room temperature, stirring for reaction for 2 h with nitrogen, ninhydrin test being negative; draining the reaction solution, performing DCM washing six times, performing MeOH contraction three times for 5 min, 5 min, and 7 min respectively, and performing vacuum drying to obtain 17.5 g of ganirelix precursor I-peptide resin.

(2) Amplification Experiment

The following steps are included: repeating the foregoing steps, and sequentially coupling Fmoc-Pro-OH, Fmoc-Lys(Boc)-OH, Fmoc-Leu-OH, Fmoc-D-Lys(Boc)-OH, Fmoc-Tyr(tBu)-OH, Fmoc-Ser(tBu)-OH, Fmoc-D-Pal-OH and Fmoc-D-Cpa-OH one by one;

dissolving Fmoc-D-Nal-OH (65.4 g, 150 mmol) and HOBt (21.3 g, 157.5 mmol) in 400 ml of DMF, adding DIC (24.7 ml, 157.5 mmol) for activating for 5 min under the condition of an ice bath, adding the activated solution to a solid-phase reaction column and stirring for reaction for 2 h with nitrogen, ninhydrin test being negative; draining the reaction solution, performing DMF washing three times, performing DBLK deprotection twice for 5 min and 7 min respectively, performing DMF washing six times, and performing DCM washing twice, ninhydrin test being positive;

dissolving acetic anhydride (10.2 g, 1000 mmol) and pyridine (79 g, 1000 mmol) in 300 ml of DCM, adding the solution to a solid-phase reaction column at room temperature, stirring for reaction for 2 h with nitrogen, ninhydrin test being negative; draining the reaction solution, performing DCM washing six times, performing MeOH contraction three times for 5 min, 5 min and 10 min respectively, and performing vacuum drying to obtain 178 g of ganirelix precursor I-peptide resin.

3. Cracking Preparation of Ganirelix Precursor I Crude Peptide to Obtain the Ganirelix Precursor I Crude Peptide (1) Small-Scale Experiment The following steps are included: adding 80 ml of lysate (TFA:Anisole:Thioanisole:EDT=90:5:3:2) frozen for 2 h to a round-bottomed flask containing 7.94 g of ganirelix precursor I-peptide resin, stirring for reaction at room temperature for 2 h, filtering, adding filtrate to 800 ml of frozen anhydrous ether, collecting solid by centrifugation, and drying to obtain 6.73 g of ganirelix acetate precursor I crude peptide with a yield of 98% and a purity of 90%.

(2) Amplification Experiment

The following steps are included: adding 1780 ml of lysate (TFA:Anisole:Thioanisole:EDT=90:5:3:2) frozen for 2 h to a round-bottomed flask containing 178 g of ganirelix precursor I-peptide resin, stirring for reaction at room temperature for 2 h, filtering, adding filtrate to 17800 ml of frozen anhydrous ether, collecting solid by centrifugation, and drying to obtain 68.5 g of ganirelix acetate precursor I crude peptide with a yield of 99.8% and a purity of 91%.

Upon detection, MS data of the ganirelix precursor I are respectively 1373.498(M+1), 1395.524(M+23) and 1411.509(M+39). The peptide spectrum is as shown in FIG. 1, wherein the retenion time of the target peak is T=16.009 min, and the purity is 90.67%.

Example 2: Synthesis of Ganirelix Precursor II-Rink Amide Peptide Resin

1. Preparation of Fmoc-D-Ala-Rink Amide Resin

The following steps are included: placing 10 g of Rink Amide resin with a substitution degree of 0.5 mmol/g into a solid-phase reaction column, performing DMF washing twice, and performing DMF swelling for 30 min and DBLK deprotection twice for 10 min and 15 min respectively, and performing DMF washing six times, ninhydrin test being positive;

dissolving Fmoc-D-Ala-OH (4.67 g, 15 mmol) and HOBt (2.13 g, 15.75 mmol) in 400 ml of DMF, adding DIC (2.47 ml, 15.75 mmol) for activating for 5 min under the condition of an ice bath, adding the activated solution to a solid-phase reaction column and stirring for reaction for 2 h with nitrogen, ninhydrin test being negative; draining the reaction solution, performing DMF washing three times, performing DBLK deprotection twice for 5 min and 7 min respectively, and performing DMF washing six times, ninhydrin test being positive.

2. Coupling of Other Amino Acids with Fmoc Protecting Group, and Obtaining Ganirelix Precursor II-Peptide Resin after Acetylation and Lysine Deprotection The following steps are included: repeating the foregoing steps, and sequentially coupling Fmoc-Pro-OH, Fmoc-Lys(Alloc)-OH, Fmoc-Leu-OH, Fmoc-D-Lys(Alloc)-OH, Fmoc-Tyr (tBu)-OH, Fmoc-Ser(tBu)-OH, Fmoc-D-Pal-OH and Fmoc-D-Cpa-OH one by one;

dissolving Fmoc-D-Nal-OH (6.54 g, 15 mmol) and HOBt (2.13 g, 15.75 mmol) in 40 ml of DMF, adding DIC (2.47 ml, 15.75 mmol) for activating for 5 min under the condition of an ice bath, adding the activated solution to a solid-phase reaction column and stirring for reaction for 2 h with nitrogen, ninhydrin test being negative; draining the reaction solution, performing DMF washing three times, performing DBLK deprotection twice for 5 min and 7 min respectively, performing DMF washing six times, and performing DCM washing twice, ninhydrin test being positive;

dissolving acetic anhydride (10.2 g, 100 mmol) and pyridine (7.9 g, 100 mmol) in 30 ml of DCM, adding the solution to a solid-phase reaction column at room temperature, stirring for reaction for 2 h with nitrogen, ninhydrin test being negative; draining the reaction solution, and performing DCM washing six times; adding 40 ml of DCM and 1.16 g of tetrakis(triphenylphosphine)palladium to the solid phase reaction column, stirring the mixture with nitrogen for 1 min, then adding 10.8 g of phenylsilane, and reacting for 0.5 h, draining, performing DMF washing six times, performing DCM washing six times, and performing MeOH contraction three times for 5 min, 5 min and 10 min respectively, and performing vacuum drying to obtain 16.9 g of the ganirelix precursor II-Rink Amide peptide resin.

Example 3: Synthesis of Ganirelix Precursor II-Rink Amide AM Peptide Resin

1. Preparation of Fmoc-D-Ala-Rink Amide AM Resin

The following steps are included: placing 8.33 g of Rink Amide AM resin with a substitution degree of 0.6 mmol/g into a solid-phase reaction column, performing DMF washing twice, and performing DMF swelling for 30 min and DBLK deprotection twice for 10 min and 15 min respectively, and performing DMF washing six times, ninhydrin test being positive;

dissolving Fmoc-D-Ala-OH (4.67 g, 15 mmol) and HOBt (2.13 g, 15.75 mmol) in 40 ml of DMF, adding DIC (2.47 ml, 15.75 mmol) for activating for 5 min under the condition of an ice bath, adding the activated solution to a solid-phase reaction column and stirring for reaction for 2 h with nitrogen, ninhydrin test being negative; draining the reaction solution, performing DMF washing three times, performing DBLK deprotection twice for 5 min and 7 min respectively, and performing DMF washing six times, ninhydrin test being positive.

2. Coupling of Other Amino Acids with Fomc Protecting Group, and Obtaining Ganirelix Precursor II-Peptide Resin after Acetylation and Lysine Deprotection The following steps are included: repeating the foregoing steps, and sequentially coupling Fmoc-Pro-OH, Fmoc-Lys(Alloc)-OH, Fmoc-Leu-OH, Fmoc-D-Lys(Alloc)-OH, Fmoc-Tyr (tBu)-OH, Fmoc-Ser(tBu)-OH, Fmoc-D-Pal-OH and Fmoc-D-Cpa-OH one by one;

dissolving Fmoc-D-Nal-OH (6.54 g, 15 mmol) and HOBt (2.13 g, 15.75 mmol) in 40 ml of DMF, adding DIC (2.47 ml, 15.75 mmol) for activating for 5 min under the condition of an ice bath, adding the activated solution to a solid-phase reaction column and stirring for reaction for 2 h with nitrogen, ninhydrin test being negative; draining the reaction solution, performing DMF washing three times, performing DBLK deprotection twice for 5 min and 7 min respectively, performing DMF washing six times, and performing DCM washing twice, ninhydrin test being positive;

dissolving acetic anhydride (10.2 g, 100 mmol) and pyridine (7.9 g, 100 mmol) in 30 ml of DCM, adding the solution to a solid-phase reaction column at room temperature, stirring for reaction for 2 h with nitrogen, ninhydrin test being negative; draining the reaction solution, and performing DCM washing six times; adding 40 ml of DCM and 1.16 g of tetrak(istriphenylphosphine)palladium to the solid phase reaction column, stirring the mixture with nitrogen for 1 min, adding 10.8 g of phenylsilane, and reacting for 0.5 h, draining, performing DMF washing six times, performing DCM washing six times, and performing MeOH contraction three times for 5 min, 5 min and 10 min respectively, and performing vacuum drying to obtain 15.3 g of the ganirelix precursor II-Rink Amide AM peptide resin.

Example 4: Synthesis of Ganirelix Precursor II-Rink Amide MBHA Peptide Resin

1. Preparation of Fmoc-D-Ala-Rink Amide MBHA Resin

The following steps are included: placing 6.67 g of Rink Amide MBHA resin with a substitution degree of 0.75 mmol/g into a solid-phase reaction column, performing DMF washing twice, and performing DMF swelling for 30 min and DBLK deprotection twice for 10 min and 15 min respectively, and performing DMF washing six times, ninhydrin test being positive;

dissolving Fmoc-D-Ala-OH (4.67 g, 15 mmol) and HOBt (2.13 g, 15.75 mmol) in 40 ml of DMF, adding DIC (2.47 ml, 15.75 mmol) for activating for 5 min under the condition of an ice bath, adding the activated solution to a solid-phase reaction column and stirring for reaction for 2 h with nitrogen, ninhydrin test being negative; draining the reaction solution, performing DMF washing three times, performing DBLK deprotection twice for 5 min and 7 min respectively, and performing DMF washing six times, ninhydrin test being positive.

2. Coupling of Other Amino Acids with Fmoc Protecting Group, and Obtaining Ganirelix Precursor II-Peptide Resin after Acetylation and Lysine Deprotection The following steps are included: repeating the foregoing steps, and sequentially coupling Fmoc-Pro-OH, Fmoc-Lys(Alloc)-OH, Fmoc-Leu-OH, Fmoc-D-Lys(Alloc)-OH, Fmoc-Tyr (tBu)-OH, Fmoc-Ser(tBu)-OH, Fmoc-D-Pal-OH and Fmoc-D-Cpa-OH one by one;

dissolving Fmoc-D-Nal-OH (6.54 g, 15 mmol) and HOBt (2.13 g, 15.75 mmol) in 40 ml of DMF, adding DIC (2.47 ml, 15.75 mmol) for activating for 5 min under the condition of an ice bath, adding the activated solution to a solid-phase reaction column and stirring for reaction for 2 h with nitrogen, ninhydrin test being negative; draining the reaction solution, performing DMF washing three times, performing DBLK deprotection twice for 5 min and 7 min respectively, performing DMF washing six times, and performing DCM washing twice, ninhydrin test being positive;

dissolving acetic anhydride(10.2 g, 100 mmol) and pyridine (7.9 g, 100 mmol) in 30 ml of DCM, adding the solution to a solid-phase reaction column at room temperature, stirring for reaction for 2 h with nitrogen, ninhydrin test being negative; draining the reaction solution, and performing DCM washing six times; adding 40 ml of DCM and 1.16 g of tetraki(striphenylphosphine)palladium to the solid phase reaction column, stirring the mixture with nitrogen for 1 min, adding 10.8 g of phenylsilane, and reacting for 0.5 h, draining, performing DMF washing six times, performing DCM washing six times, and performing MeOH contraction three times for 5 min, 5 min and 10 min respectively, and performing vacuum drying to obtain 14.1 g of the ganirelix precursor II-Rink Amide MBHA peptide resin.

Example 5: Synthesis of Crude Ganirelix

The following steps are included: dissolving the ganirelix precursor I (2.748 g, 2 mmol) that are obtained in Example land triethylamine (1.215 g, 12 mmol) in 40 ml of DMF, dropwise adding a DMF solution containing 20 ml of ethylamino ethylimino methanesulfonic acid (1.44 g, 8 mmol) slowly under the condition of an ice bath, after completing adding, restoring to room temperature for reacting for 24 h, HPLC showing that the raw materials are completely reacted; adding the reaction solution to ice water in an amount 10 times that of the reaction solution under stirring, collecting the solid by filtration and washing three times with anhydrous ether, and performing vacuum drying to obtain 3.04 g of crude ganirelix with a purity of 80% and a yield of 97%.

Example 6: Synthesis of Crude Ganirelix

The following steps are included: dissolving ganirelix precursor I (2.748 g, 2 mmol) that are obtained in Example 1 and DIPEA (1.55 g, 12 mmol) in 40 ml of NMP, dropwise adding an NMP solution containing 20 ml of ethylamino ethylimino methanesulfonic acid (1.44 g, 8 mmol) slowly under the condition of an ice bath, after completing adding, restoring to room temperature for reacting for 24 h, HPLC showing that the raw materials are completely reacted; adding the reaction solution to ice water in an amount 10 times that of the reaction solution under stirring, collecting the solid by filtration and washing three times with anhydrous ether, and performing vacuum drying to obtain 2.89 g of crude ganirelix with a purity of 76% and a yield of 92%.

Example 7: Synthesis of Crude Ganirelix

The following steps are included: dissolving ganirelix precursor I (2.748 g, 2 mmol) that are obtained in Example 1 and TMP (1.45 g, 12 mmol) in 40 ml of DMSO, dropwise adding a DMSO solution containing 20 ml of ethylamino ethylimino methanesulfonic acid (1.44 g, 8 mmol) slowly under the condition of an ice bath, after completing adding, restoring to room temperature for reacting for 24 h, HPLC showing that the raw materials are completely reacted; adding the reaction solution to ice water in an amount 10 times that of the reaction solution under stirring, collecting the solid by filtration and washing three times with anhydrous ether, and performing vacuum drying to obtain 3.14 g of crude ganirelix with a purity of 78% and a yield of 100%.

Example 8: Synthesis of Crude Ganirelix

The following steps are included: dissolving ganirelix precursor I (2.748 g, 2 mmol) that are obtained in Example 1 and pyridine (0.95 g, 12 mmol) in 40 ml of acetonitrile, dropwise adding an acetonitrile solution containing 20 ml of ethylamino ethylimino methanesulfonic acid (1.44 g, 8 mmol) slowly under the condition of an ice bath, after completing adding, restoring to room temperature for reacting for 24 h, HPLC showing that the raw materials are completely reacted; adding the reaction solution to ice water in an amount 10 times that of the reaction solution under stirring, collecting the solid by filtration and washing three times with anhydrous ether, and performing vacuum drying to obtain 2.99 g of crude ganirelix with a purity of 61% and a yield of 95%.

Example 9: Synthesis of Crude Ganirelix

The following steps are included: adding 40 ml of THF to a reaction flask containing the ganirelix precursor I (2.748 g, 2 mmol) that are obtained in Example 1 and $NaHCO_3$ (1.01 g, 12 mmol), dropwise adding a THF solution containing 20 ml of ethylamino ethylimino methanesulfonic acid (1.44 g, 8 mmol) slowly under the condition of an ice bath, after completing adding, restoring to room temperature for reacting for 24 h, HPLC showing that the raw materials are completely reacted; adding the reaction solution to ice water in an amount 10 times that of the reaction solution under stirring, collecting the solid by filtration and washing three times with anhydrous ether, and performing vacuum drying to obtain 2.74 g of crude ganirelix with a purity of 57% and a yield of 87%.

Example 10: Synthesis of Crude Ganirelix

The following steps are included: adding 40 ml of 1,4-dioxane to a reaction flask containing the ganirelix precursor I (2.748 g, 2 mmol) that are obtained in Example 1 and $Na_2CO_3$ (1.272 g, 12 mmol), dropwise adding a 1,4-dioxane solution containing 20 ml of ethylamino ethylimino methanesulfonic acid (1.44 g, 8 mmol) slowly under the condition of an ice bath, after completing adding, restoring to room temperature for reacting for 24 h, HPLC showing that the raw materials are completely reacted; adding the reaction solution to ice water in an amount 10 times that of the reaction solution under stirring, collecting the solid by filtration and washing three times with anhydrous ether, and performing vacuum drying to obtain 3.08 g of crude ganirelix with a purity of 55% and a yield of 98%.

Example 11: Synthesis of Crude Ganirelix

The following steps are included: adding 40 ml of MeOH to a reaction flask containing the ganirelix precursor I (2.748 g, 2 mmol) that are obtained in Example 1 and $Na_2CO_3$ (1.153 g, 12 mmol), dropwise adding a MeOH solution containing 20 ml of ethylamino ethylimino methanesulfonic acid (1.44 g, 8 mmol) slowly under the condition of an ice bath, after completing adding, restoring to room temperature for reacting for 24 h, HPLC showing that the raw materials are completely reacted; adding the reaction solution to ice water in an amount 10 times that of the reaction solution under stirring, collecting the solid by filtration and washing three times with anhydrous ether, and performing vacuum drying to obtain 2.95 g of crude ganirelix with a purity of 59% and a yield of 94%.

Example 12: Synthesis of Crude Ganirelix

The following steps are included: adding 100 ml of DMF and triethylamine (5.06 g, 50 mmol) to a round-bottomed flask containing the ganirelix precursor II-Rink Amide resin (16.9 g, 5 mmol) obtained in Example 2, dropwise adding a DMF solution containing 50 ml of ethylamino ethylimino methanesulfonic acid (5.4 g, 30 mmol) slowly under the condition of an ice bath, after completing adding, restoring to room temperature and stirring for reacting for 24 h; transferring the reaction solution to a solid-phase reaction column, draining the reaction solution, performing DMF washing on the resin six times, performing DCM washing twice, performing MeOH contraction three times for 5 min, 5 min and 10 min respectively, and performing vacuum drying to obtain 17.6 g of ganirelix peptide resin; adding 200 ml of frozen lysate (TFA:Anisole:Thioanisole:EDT=90:5:3:2) to a round-bottomed flask containing ganirelix peptide resin, stirring for reacting for 2 h at room temperature, filtering, and adding the filtrate to 2 l of frozen anhydrous ether, collecting the solid by centrifugation, washing the solid three times with anhydrous ether, and performing vacuum drying to obtain 7.4 g of crude ganirelix with a purity of 82% and a yield of 95%.

Example 13: Synthesis of Crude Ganirelix

The following steps are included: adding 100 ml of DMF and triethylamine (5.06 g, 50 mmol) to a round-bottomed flask containing the ganirelix precursor II-Rink Amide AM resin (15.3 g, 5 mmol) obtained in Example 3, dropwise adding a DMF solution containing 50 ml of ethylamino ethylimino methanesulfonic acid (5.4 g, 30 mmol) slowly under the condition of an ice bath, after completing adding, restoring to room temperature and stirring for reacting for 24 h; transferring the reaction solution to a solid-phase reaction column, draining the reaction solution, performing DMF washing on the resin six times, performing DCM washing twice, performing MeOH contraction three times for 5 min, 5 min and 10 min respectively, and performing vacuum drying to obtain 16.7 g of ganirelix peptide resin; adding 170 ml of frozen lysate (TFA:Anisole:Thioanisole:EDT=90:5:3:2) to a round-bottomed flask containing the ganirelix peptide resin, stirring for reacting for 2 h at room temperature, filtering, and adding the filtrate to 1.7 l of frozen anhydrous ether, collecting the solid by centrifugation, washing the solid three times with anhydrous ether, and performing vacuum drying to obtain 7.2 g of crude ganirelix with a purity of 81.7% and a yield of 91.7%.

Example 14: Synthesis of Crude Ganirelix

The following steps are included: adding 100 ml of DMF and triethylamine (5.06 g, 50 mmol) to a round-bottomed flask containing the ganirelix precursor II-Rink Amide MBHA resin (14.1 g, 5 mmol) obtained in Example 4, dropwise adding a DMF solution containing 50 ml of ethylamino ethylimino methanesulfonic acid (5.4 g, 30 mmol) slowly under the condition of an ice bath, after completing adding, restoring to room temperature and stirring for reacting for 24 h; transferring the reaction solution to a solid-phase reaction column, draining the reaction solution, performing DMF washing on the resin six times, performing DCM washing twice, performing MeOH contraction three times for 5 min, 5 min and 10 min respectively, and performing vacuum drying to obtain 15.1 g of ganirelix peptide resin; adding 150 ml of frozen lysate (TFA:Anisole:Thioanisole:EDT=90:5:3:2) to a round-bottomed flask containing the ganirelix peptide resin, stirring for reacting for 2 h at room temperature, filtering, and adding the filtrate to 1.5 l of frozen anhydrous ether, collecting the solid by centrifugation, washing the solid three times with anhydrous ether, and performing vacuum drying to obtain 7.3 g of crude ganirelix with a purity of 81.6% and a yield of 93%.

Example 15: Preparation of Pure Ganirelix Acetate

1. Sample Treatment
The following steps are included: dissolving the solid crude peptide in 25% acetonitrile/75% water (V/V), completely dissolving the sample by ultrasonic, filtering by using a filter membrane, and collecting filtrate for later use.
2. HPLC Purification
(1) Purification Conditions
Chromatographic column: the diameter and the length of a chromatographic column employing octylsilane-bonded silica as a stationary phase is 50 mm×250 mm.
Mobile phase: the phase A is a 20 mM sodium perchlorate solution, pH is adjusted to 1.5 with phosphoric acid; the phase B is acetonitrile; the flow rate is 80 ml/min; gradient elution is performed with a mobile phase varying from 75% A+25% B to 65% A+35% B; the detection wavelength is 280 nm; and the sample size is 2 g.
(2) Purification Process
The following steps are included: setting samples after equilibrating the chromatographic column for 5 min, operating gradient purification, monitoring and collecting target peak fractions before the peak, at the peak and after the peak; recycling and purifying the fractions before and after the peak after the removal of most of the acetonitrile; and performing salt conversion treatment on the fraction at the peak after the removal of most of the acetonitrile.
3. Salt Conversion Treatment
(1) Treatment Conditions
Chromatographic column: the diameter and the length of a chromatographic column employing a reverse phase C8 chromatographic packing as a stationary phase is 50 mm×250 mm.
Mobile phase: the phase A is a 0.20% glacial acetic acid (V/V) solution; the phase B is chromatographic grade acetonitrile; and after gradient elution is performed with 95% A+5% B serving as a mobile phase for 20 min, the mobile phase is varied from 95% A+5% B to 50% A+50% B within 2 min, and then gradient elution is performed with 50% A+50% B serving as a mobile phase; a detection wavelength is 280 nm; and a sample volume injected is 200 ml.
(2) Treatment Process
The following steps are included: setting samples after equilibrating the chromatographic column for 5 min, operating gradient purification, monitoring and collecting target peak fractions; concentrating the target peak fractions to 20 ml by reduced-pressure rotary distillation and performing lyophilization to obtain 0.64 g of white solid powdery pure peptide, with a purity of 99.71%, all single impurities of less than 0.1%, a purification yield of 72.2% (calculated by the content of ganirelix acetate in the crude product), and a total yield of 26.1%.

Figure 2:
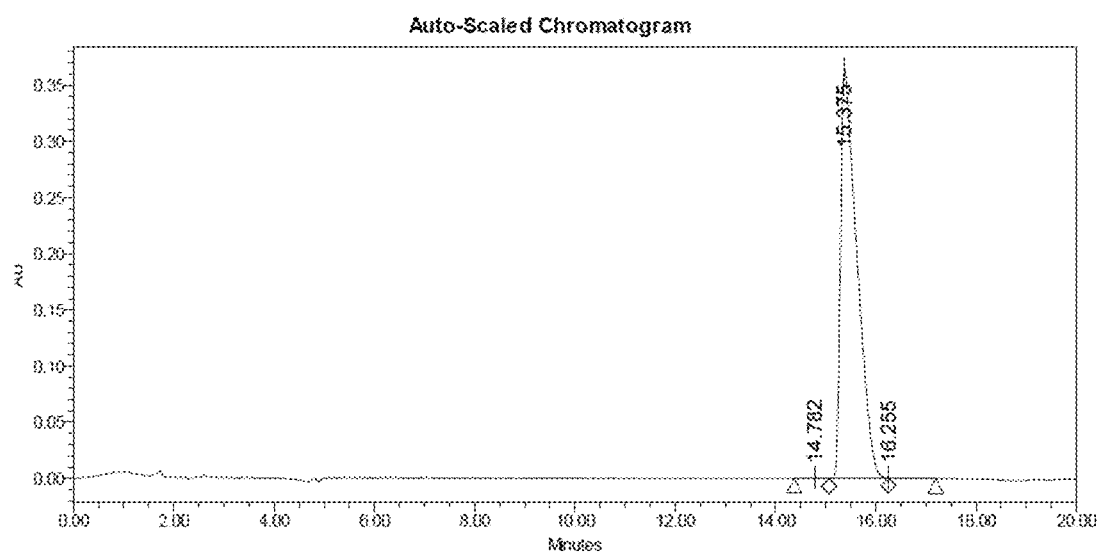
FIG. 2 is a precise peptide spectrum of pure ganirelix acetate prepared from example 15.

Upon detection, MS of pure peptide after purification of the ganirelix acetate is 1570.862(M+1). The pure peptide spectrum is as shown in FIG. 2, wherein the retenion time of the target peak is T=15.357 min, and the purity is 99.80%.

What is claimed is:
1. A ganirelix precursor I having a structure as shown below:
Ac-D-2-Nal-D-Phe(4-Cl)-D-3-Pal-Ser-Tyr-D-Lys-Leu-Lys-Pro-D-Ala-$NH_2$.

2. A method for preparing the ganirelix precursor I of claim 1, comprising the following steps:
  (1) reacting Fmoc-D-Ala-OH with a resin to obtain a Fmoc-D-Ala-resin;
  (2) coupling the Fmoc-D-Ala-resin to the other amino acids with Fmoc protecting group one by one, followed by acetylation, to obtain a ganirelix precursor I-peptide resin; and
  (3) subjecting the ganirelix precursor I-peptide resin to a cleavage reaction to obtain the ganirelix precursor I.

3. The method of claim 2, wherein the other amino acids with Fmoc protecting group in step (2) are Fmoc-Pro-OH, Fmoc-Lys(Boc)-OH, Fmoc-Leu-OH, Fmoc-D-Lys(Boc)-OH, Fmoc-Tyr(tBu)-OH, Fmoc-Ser(tBu)-OH, Fmoc-D-Pal-OH, Fmoc-D-Cpa-OH and Fmoc-D-Nal-OH, respectively.

4. The method of claim 2, wherein the resin is Rink Amide resin, Rink Amide AM resin or Rink Amide MBHA resin.

5. The method of claim 2, wherein the ratio of cleavage reagents employed in the cleavage reaction in step (3) or step (2) is trifluoric acetic acid (TFA):Anisole:Thioanisole:triisoproplysilane (TIS):water ($H_2O$):1,2 ethanedithiol (EDT)=90-95:0-5:0-3:0-3:0-5:0-2(V/V).

6. The method of claim 5, wherein the cleavage reagents employed is trifluoroacetic acid (TFA):Anisole:Thioanisole: 1,2 ethanedithiol (EDT)=90:5:3:2(V/V).

7. A method for preparing ganirelix acetate, comprising the following steps:
  (1) preparing the ganirelix precursor I of claim 1;
  (2) performing modifications on side chain amino groups of Lys and D-Lys of the ganirelix precursor I obtained in step (1) to obtain crude ganirelix; and
  (3) subjecting the crude ganirelix obtained in step (2) to purification, salt conversion and lyophilization to obtain pure ganirelix acetate.

8. The method of claim 7, wherein a reagent used for performing modifications on side chain amino groups in step (2) is ethylamino ethylimino methanesulfonic acid,
  a solvent used in step (2) is N,N-dimethylformamide (DMF), N-methylpyrrolidone (NMP), dimethyl sulfoxide (DMSO), acetonitrile, tetrahydrofuran (THF), 1,4-dioxane or methanol (MeOH), and
  a base used in step (2) is N,N-diisopropylethylamine (DIPEA), triethylamine ($Et_3N$), 2,2,6,6-tetramethylpiperidine (TMP), pyridine, sodium bicarbonate ($NaHCO_3$) or sodium carbonate ($Na_2CO_3$).

9. The method of claim 7, wherein the purification in step (3) is high performance liquid chromatography (HPLC).

10. The method of claim 9, wherein the HPLC purification comprises the following specific steps: performing gradient elution with a mobile phase varying from 75% A+25% B to 65% A+35% B, wherein a stationary phase of a chromatographic column is octylsilane-bonded silica, mobile phase A is 20 mM sodium perchlorate solution in which pH has been adjusted to 1.5 using phosphoric acid, and mobile phase B is acetonitrile.

11. The method of claim 7, wherein the salt conversion comprises the following specific steps: elution with 95% A+5% B for 20 mins followed by varying the mobile phase from 95% A+5% B to 50% A+50% B within 2 mins, and then gradient elution with 50% A+50% B, wherein, a stationary phase of the chromatographic column is a reverse phase C8 chromatographic packing, mobile phase A is 0.20% glacial acetic acid (V/V) solution, and mobile phase B is chromatography grade acetonitrile.

12. A ganirelix precursor II-peptide resin having a structure as shown below:

Ac-D-2-Nal-D-Phe(4-Cl)-D-3-Pal-Ser(tBu)-Tyr(tBu)-D-Lys-Leu-Lys-Pro-D-Ala-resin.

13. A method for preparing the ganirelix precursor II-peptide resin of claim 12, comprising the following steps:
  (1) reacting Fmoc-D-Ala-OH with a resin to obtain a Fmoc-D-Ala-resin; and
  (2) coupling the Fmoc-D-Ala-resin to other amino acids with Fmoc protecting group one by one, followed by acetylation and lysine deprotection, to obtain a ganirelix precursor II-peptide resin.

14. The method of claim 13, wherein the other amino acids with Fmoc protecting group in step (2) are Fmoc-Pro-OH, Fmoc-Lys(Alloc)-OH, Fmoc-Leu-OH, Fmoc-D-Lys (Alloc)-OH, Fmoc-Tyr(tBu)-OH, Fmoc-Ser(tBu)-OH, Fmoc-D-Pal-OH, Fmoc-D-Cpa-OH and Fmoc-D-Nal-OH, respectively.

15. The method of claim 13, wherein the resin is Rink Amide resin, Rink Amide AM resin or Rink Amide MBHA resin.

16. A method for preparing ganirelix acetate, comprising the following steps:
  (1) preparing the ganirelix precursor II-peptide resin of claim 12;
  (2) performing modifications on side chain amino groups of Lys and D-Lys of the ganirelix precursor II-peptide resin prepared in step (1), and subjecting the ganirelix precursor II-peptide resin to a cleavage reaction to obtain crude ganirelix; and
  (3) subjecting the crude ganirelix obtained in step (2) to purification, salt conversion and lyophilization to obtain pure ganirelix acetate.

17. The method of claim 16, wherein a reagent used for performing modifications on side chain amino groups in step (2) is ethylamino ethylimino methanesulfonic acid, a solvent used is N,N-dimethylformamide (DMF), dichloromethane (DCM) or dimethyl sulfoxide (DMSO), and a base used is N,N-diisopropylethylamine (DIPEA), triethylamine ($Et_3N$) or N-methylmorpholine (NMM).

18. The method of claim 16, wherein the ratio of cleavage reagents in the cleavage reaction in step (3) or step (2) is trifluoroacetic acid (TFA):Anisole:Thioanisole:thiisopropylsilane (TIS):water ($H_2O$):1, 2-ethanedithiol (EDT)=90-95: 0-5:0-3:0-3:0-5:0-2(V/V);
  or the cleavage reagents employed is trifluoroacetic acid (TFA):Anisole:Thioanisole:1,2-ethanedithiol (EDT)=90:5:3:2(V/V).

19. The method of claim 16, wherein the purification in step (3) is high performance liquid chromatography (HPLC);
  or the purification in step (3) is the HPLC that comprises the following specific steps: performing gradient elution with a mobile phase varying from 75% A+25% B to 65% A+35% B, wherein a stationary phase of the chromatographic column is octylsilane-bonded silica, mobile phase A is 20 mM sodium perchlorate solution in which pH has been adjusted to 1.5 using phosphoric acid, and mobile phase B is acetonitrile.

20. The method of claim 16, wherein the salt conversion comprises the following specific steps: elution with 95% A+5% B served as a mobile phase for 20 mins and followed by varying the mobile phase from 95% A+5% B to 50% A+50% B within 2 mins, and then gradient elution with 50% A+50% B served as a mobile phase, wherein, a stationary phase of the chromatographic column is a reverse phase C8 chromatographic packing, mobile phase A is 0.20% glacial acetic acid (V/V) solution, and mobile phase B is chromatographic grade acetonitrile.

* * * * *